United States Patent
Gorewit

(12) 
(10) Patent No.: US 6,391,362 B1
(45) Date of Patent: May 21, 2002

(54) BULK PREPARATION OF MILK FAT GLOBULE MEMBRANES

(76) Inventor: Ronald C. Gorewit, 68 Hunt Hill Rd., Ithaca, NY (US) 14850

( * ) Notice: Subject to any disclaimer, the term of this patent is extended or adjusted under 35 U.S.C. 154(b) by 0 days.

(21) Appl. No.: 09/714,423

(22) Filed: Nov. 16, 2000

Related U.S. Application Data

(60) Continuation-in-part of application No. 09/236,906, filed on Jan. 25, 1999, which is a division of application No. 08/703,776, filed on Aug. 27, 1996, now Pat. No. 5,905,026.
(60) Provisional application No. 60/165,826, filed on Nov. 16, 1999.

(51) Int. Cl.$^7$ ............................................... A23C 1/00
(52) U.S. Cl. ....................................................... 426/491
(58) Field of Search ................................ 426/491, 495, 426/586, 656; 530/366, 369, 386, 412, 481, 359

(56) References Cited

U.S. PATENT DOCUMENTS 4,997,668 A  3/1991  Johnson et al. ............. 426/580

FOREIGN PATENT DOCUMENTS

| EP | 0494654 | 7/1992 |
| JP | 04244020 | 9/1992 |
| JP | 05030942 | 9/1993 |

OTHER PUBLICATIONS

Darling et al. "Milk–fat globule membrane in homogenized cream" Journal of Dairy Research, vol. 45 No. 2, pp. 197–208 (with pictures), Feb. 1978.

McPherson et al. "Isolation of bovine milk fat globule membrane material from cream without prior removal of caseins and whey proteins" Journal of Dairy Research, vol. 51 No. 1, pp. 113–121, Jan. 1984.

Chandan et al. "Physicochemical Analyses of Bovine Milk Fat Globule Membrane. I. Different Thermal Analysis" Journal of Dairy Science, vol. 54 No. 12, pp. 1744–1751, Dec. 1971.

Dion et al. "Human Milk Fat Globule Membrane Glycoproteins Express Group–Related Determinants Primarily On Mucin–Like Epithelial Membrane Antigens and gp70" Biochemistry Int., vol. 22 No. 2, pp. 295–302, Feb. 1990.

Palmquist et al. Dietary Fat Composition Influences Fatty Acid Composition of Milk Fat Globule Membrane in Lactating Cow LIPIDS, vol. 26 No. 9, pp. 718–722, Sep. 1991.

Adachi et al. "Possibility of Lymphatic Absorption of Epidermal Growth Factor from Intestine" Yakugaku Zasshi vol. 113 No. 3, pp. 256–263, Mar. 1993.

*Primary Examiner*—Keith Hendricks
(74) *Attorney, Agent, or Firm*—Webb Ziesenheim Logsdon Orkin & Hanson, P.C.

(57) ABSTRACT

A bulk preparation method for isolating milk fat globule membranes from milk in which the separation method is the same whether the milk fat globule membranes are collected in bulk in the dairy industry or collected for an individual patient for diagnostic purposes. The method includes the steps of channeling the desired quantity of unhomogenized milk through a pasteurizer (high temperature, short time) and whipping the milk thus pasteurized into two phases. Phase 1 is the cream phase and phase 2 is the first aqueous phase. The cream phase is separated from the first aqueous phase and is washed with distilled or sterile water at about 37 degrees Celsius for approximately 24 hours to create a second aqueous phase, which is then filtered and dried (by spray drying or lyophilization, for example) to create a solid milk fat globule membrane product.

9 Claims, No Drawings

BULK PREPARATION OF MILK FAT GLOBULE MEMBRANES

RELATED APPLICATIONS

The present invention is a continuation-in-part application based on U.S. application Ser. No. 09/236,90 affirmed Jan. 25, 1999, and also claims the benefit of the filing date of U.S. Provisional Application Ser. No. 60/165,826 filed Nov. 16, 1999; said 09/236,906 is a divisional of U.S. application Ser. No. 08/703,776, now U.S. Ser. No. 5,905,026 filed Aug., 27, 1996.

FIELD OF THE INVENTION

Milk fat globule membranes are diagnostically, pharmaceutically and nutriceutically useful proteo-lipid compositions, and the present invention provides for their bulk separation from milk.

BACKGROUND OF THE INVENTION

One remarkable feature of milk is the presence of lipid droplets coated with proteo-lipid material, or, as it is usually referred to as the milk fat globule membrane (MFGM). The MFGM is composed of four layers: the thin membrane, possibly derived from intracellular lipovesicles; the protein coat; the lipid bilayer, primarily derived from the apical plasma membrane and possibly secretory vesicle membranes; and the glycocalyx. Milk protein synthesis during lactation is simultaneously accomplished by the intensive synthesis of membrane components needed to replenish their loss by their extrusion from mammary gland secretory cells. In this sense, milk is a unique deposit of biological membranes synthesized inside secretory epithelial cells.

The study of MFGM proteins has received much attention over the years. Many proteins of the MFGM have been well characterized. Some of the genes encoding these proteins have been cloned. Certain proteins of the MFGM are of special interest because of their involvement in important cellular processes. Milk fat globule membrane (MFGM) contains large quantities of the novel proteins and factors that play physiological roles such as inhibiting the growth of cancer cells, increasing the growth and proliferation of normal cells and lowering blood cholesterol. Two specific proteins in the milk fat globule membranes are MDGI/FABP [mammary derived growth inhibitor (MDGI or FABP (fatty acid binding protein)] a 15 kDa protein and BRCA1/BRCA2 (breast ovarian cancer susceptibility protein). BRCA1 is a tumor supressor protein that is also involved in cell signaling, DNA repair and apoptosis.

Several experiments have been conducted to illuminate the physiological mechanism whereby milk fat derived MDGI/FABP inhibits the growth of mammary cells. One of the experiments has proven that MDGI/FABP is in a phosphorylated form when it is present in mammary cells. The MDGI/FABP is phosphorylated on tyrosine. It is believed that the physiological activity of MDGI/FABP is regulated through its phosphorylation by protein kinases. Protein kinase activity exists in the milk fat globule membranes obtained from bovine and human milk.

Other experiments designed to determine the mechanism of MDGI/FABP on mammary cell growth and differentiation have led to the discovery that MDGI/FABP is in close association with the glycoprotein CD36 within the MFGM. CD36 is an abundant protein found in milk fat from cows. It is involved in cellular differentiation, lipid transport and sequestering oxidized fatty acids in milk. The information currently available suggests that the inhibitory action of MDGI/FABP and its synthetic analogs on cell proliferation is manifested through their interaction with the ectodomain of CD36. Moreover, CD36 may be a receptor for MDGI/FABP.

It has been suggested that the variation in fatty acids in adipocytes extracted from premenopausal and post menopausal women can act directly on growth and differentiation of mammary epithelial cells and the variation of CD36 may act either on the transport of fatty acids or on the transduction of the signal responsible for the stimulation of enzymes catalyzing the conversion of fatty acid into different metabolites.

CD 36 expression is elevated in various primary human breast tumors. Diets high in saturated fats may influence the synthesis of CAMs such as CD36, thereby making certain tissues such as the mammary tissue more susceptible to carcinogens.

Unsaturated long chain fatty acids may also regulate levels of CD36. Heart type fatty acid binding protein is increased in mammary tumors, propagated in nude mice, in response to either unsaturated or saturated fatty acids.

It has also been recently demonstrated that two genes, namely, BRCA1 encoding a 220 kDa protein, and BRCA2 encoding an approximate 420 kDa protein, are involved in hereditary breast and ovarian cancers. The BRCA1 protein contains an N-terminus zinc finger domain, i.e. the region which can bind to DNA. The BRCA1 protein may represent one of the transcription factors, playing an important role in the differentiation of mammary gland cells. The C-terminal end of the BRCA1 is essential to normal BRCA1 function in breast epithelial cells, because patients inheriting 1853Stop develop very early onset breast cancer. The development of hereditary breast cancers can be seen as the result of mutations or deletions of the BRCA1 gene leading to the production of altered forms (truncated) of BRCA1 protein which cannot function as suppressors of cell growth (tumor suppressors).

It has been shown that the BRCA1 protein also can be involved in sporadic breast cancers. In this case, the transport of BRCA1 protein into the nucleus of cell is believed to be altered. Therefore, an accumulation of BRCA1 protein occurs in the cytoplasm of mammary gland secretory cells. Although there is some controversy regarding this hypothesis, the result cannot be ignored. It has been reported that the expression of BRCA1 in sporadic cancers is diminished. Quite recently, it was reported that BRCA1 is a secreted protein. Clustered BRCA1 proteins were detected by immunogold electron microscopy in small membrane bound vesicles in the apical cytoplasm of mammary epithelial cells. BRCA1has also been localized in bovine mammary epithelial cells from lactating cows. It is suggested that BRCA1 can manifest its function through the secretion and subsequent binding to the putative receptor of the same cell.

Though there is no consensus on the mechanism of action of BRCA1we have to accept that BRCA1 is an important protein for development and differentiation of mammary gland secretory epithelial cells. Mutations or microdeletions of the BRCA1 gene or altered expression of BRCA1 mRNA and BRCA1 protein can lead to dedifferentiation with possible formation of cancer cells.

Recently, the complete sequence of the BRCA2 gene was reported. This gene encodes the protein of 3418 amino acids i.e. this protein would be about 420 kDas. Biochemical function of BRCA2 is not yet clear though the presence of regulatory signals are indicated. A mutational profile of BRCA2 differs from BRCA1 and is characterized by microdeletions rather than point mutations. The microdeletions in BRCA2 gene would explain the truncated forms of the BRCA2protein. The 15 mutations observed so far by the Myriad group are quite distinct. This situation can complicate the development of the genetic test for the determination of predisposition to breast cancer. BRCA2 as BRCA1 has a sequence ("granin consensus") which is typical for a number of secretory proteins. The secretion of BRCA2 protein by mammary epithelial cells still has to be determined.

The protein BRCA1 is produced in mammary cells, but isolating BRCA1 from mammary cells is expensive and time consuming, such that it is entirely impractical to isolate commercial quantities of BRCA1. Therefore, it will be extremely important to develop an inexpensive method of isolating BRCA1 if it is to be used as a treatment.

Butyrophilin (Bph) is a 62–67 kDa glycoprotein found in the MFGM. It is the major glycoprotein of the bovine MFGM accounting for over 40 and 50% of the total protein on a weight and molar bases, respectively. Bph is specifically expressed in bovine mammary tissue. Bph is abundant only during lactation in secretory epithelial cells.

Bph has been detected in the apical pole of the secretory epithelial cell during budding of fat droplets. Butyrophilin protein and its transcripts have only been detected in the MFGM and mammary secretory epithelial cell and not in any other tissue or cell studied. It can therefore be considered as an organ specific protein.

The Bph gene is clearly regulated developmentally in the mammary gland with maximal expression during lactation. The amounts of bovine Bph mRNA increase dramatically in the last 6 wk of pregnancy and mouse. Bph mRNA is detectable from mid to late pregnancy.

It has been suggested that Bph is involved in the secretion of milk fat globule membranes and that fatty acids may be esterified to butryophilin.

Recent evidence suggests that Bph may be involved in immune recognition. Since the Bph gene has been localized to human chromosome 6p21.3–6p22 within the region encompassing class 1 genes of the major histocompatability complex.

One of the remarkable features of milk is its content of lipid droplets coated with proteo-lipid material. These droplets are milk fat globule membranes (MFGM). The MFGM is composed of four layers: the thin membrane, possibly derived from intracellular lipovesicles; the protein coat; the lipid bilayer, primarily derived from the apical plasma membrane and possibly secretory vesicle membranes; and the glycocalyx. Electron microscopy of the MFGM revealed that a major component of it represents membranous sheets with associated coat material; however, some MFGM also appeared as vesicles with little or no coat material. It is very likely that the synthesis of milk proteins during lactation is simultaneously accomplished by intensive synthesis of the above mentioned membrane components needed to replenish their loss by their extrusion from mammary gland secretory cells. In this sense, milk is a unique depot of the biological membranes synthesized inside the mammary secretory epithelial cells.

Completely apart from BRCA1 and BRCA2 assays, MFGMs have other properties which make them desirable as pharmaceuticals, nutriceuticals, food additives and excipients. A need remains for a commercially viable method for preparing bulk quantities of MFGMs in a manner suitable for their further use in pharmaceutical compositions, nutriceuticals and foodstuffs.

SUMMARY OF THE INVENTION

The present invention is a bulk preparation method for isolating milk fat globule membranes from milk. When the method is used for preparing milk fat globule membranes in the dairy industry, the process is used with large starting quantities of whole milk. When milk fat globule membranes are collected from a human patient for BRCA1 and BRCA2 assays, the quantity of milk is much smaller, i.e., 100–200 ml. The separation method is the same, however, whether the milk fat globule membranes are collected in bulk in the dairy industry or collected for an individual patient for diagnostic purposes. The method includes the steps of channeling the desired quantity of milk through a pasteurizer (high temperature, short time) and whipping the milk thus pasteurized into two phases, without prior homogenization. Phase 1 is the cream phase and phase 2 is the first aqueous phase. The cream phase is separated from the first aqueous phase and is washed with distilled or sterile water at about 4 degrees Celsius for approximately 24 hours to create a second aqueous phase. The second aqueous phase is collected and passed through a microfilter device to remove lactose, and after lactose removal the remaining aqueous phase is lyophilized or spray-dried or vitrified to prepare a solid concentrated preparation of milk fat globule membranes.

DETAILED DESCRIPTION OF THE INVENTION

The present invention is a bulk preparation method for isolating milk fat globule membranes from milk. When the method is used for preparing milk fat globule membranes in the dairy industry, the process is used with large starting quantities of whole milk. When milk fat globule membranes are collected from a human patient for BRCA1 and BRCA2 assays, the quantity of milk is much smaller, i.e., 100–200 ml. The separation method is the same, however, whether the milk fat globule membranes are collected in bulk in the dairy industry or collected for an individual patient for diagnostic purposes. The method includes the steps of channeling the desired quantity of milk through a pasteurizer (high temperature, short time) and whipping the milk thus pasteurized into two phases, without prior homogenization. Phase 1 is the cream phase and phase 2 is the first aqueous phase. The cream phase is separated from the first aqueous phase and is washed with distilled or sterile water at about 4 degrees Celsius for approximately 24 hours to create a second aqueous phase. The second aqueous phase is collected and passed through a microfilter device to remove lactose, and after lactose removal the remaining aqueous phase is lyophilized or spray-dried or vitrified to prepare a solid concentrated preparation of milk fat globule membranes.

The BRCA1 and BRCA2 proteins, products of Breast Cancer 1 gene and Breast Cancer 2 gene respectively, play an important role in a development and differentiation of mammary gland epithelial cells. These proteins are considered repressors of cell growth Genetic alterations of BRCA1 and BRCA2 genes, and consequently, the alterations of BRCA1 and BRCA2 proteins can lead to development of breast cancer. The analysis of BRCA1 and BRCA2 genes and, or their products can be used for diagnostic purposes. The genetic material, like DNA of blood cells, can be easily obtained for the screening of the BRCA1/BRCA2 genes whereas the appropriate material of BRCA1/BRCA2 proteins for their direct diagnostic analysis can be obtained only via biopsy.

One of the discoveries of the present invention is the presence of immunoreactive BRCA1 protein (about 220 kDa) in human milk fat globule membrane (MFGM). Thus, MFGM can be used as a source for the analysis of the BRCA1 protein. Mutations, microdeletions and decreased expression of BRCA1 will lead to the accumulation of this protein in MFGM in the form of truncated polypeptides or in diminished amount. The same is true about the BRCA2 protein. A method for the analysis of the BRCA1 and BRCA2 proteins in human MFGM is described herein. This analysis includes a test for identification of women with predisposition to breast cancer.

This invention increases the ease of obtaining in vivo sources of BRCA1 and BRCA2 proteins, products of Breast Cancer 1 gene and Breast Cancer 2 gene respectively. Only 100–200 ml of milk is needed to get the sufficient amount of MFGM for analysis of BRCA1 and BRCA2 proteins. Analysis of these proteins by Western immunoblotting and/or by peptide mapping can show the abnormalities in their synthesis, i.e., expression, and/or in their primary structure as a result of deletions or mutations. This test is not invasive to the patient and is easier than a genetic test. Furthermore, by analyzing the expressed protein, one can also pick up phenotypic changes in the proteins caused by changes in control genes and other genes that may still be undiscovered yet and have an affect on the BRCA1 and BRCA2 proteins. Therefore, the present invention is an important development in the evaluation of predisposition to breast cancer.

The presence of immunoreactive BRCA1 protein (about 220 kDa) in human and bovine milk fat globule membranes (MFGM) supports the idea that this protein is secretory protein. However, it does not exclude the idea that BRCA1 can function as a suppressor. In any circumstance, the detection and subsequent analysis of BRCA1 in human milk samples, i.e. in MFGM, would provide valuable information regarding the expression of BRCA1 protein in mammary gland cells. It is possible to imagine that such an analysis could become the basis for development of a test for the identification of individuals with predisposition to breast cancer and maybe to ovarian cancer. Similar ideas are applicable to the analysis of BRCA2 in human MFGM.

MFGM originates from the apical plasma membrane of mammary gland epithelial cells. The protein composition of the MFGM was studied for many years. It has recently been demonstrated that the MFGM possesses intrinsic protein phosphorylation. A number of protein kinases were detected in MFGM and the novel protein kinase butyrophilin-kinase (Bph-kinase) was proposed as a main kinase in these membranes. Among the in vitro phosphorylated proteins of the human and bovine MFGM, there is phosphorylated 220 kDa protein corresponding to the position of immunoreactive BRCA 1. Therefore, the protein kinase phosphorylating the 220 kDa protein is present in MFGM.

Since the BRCA1 and BRCA2 proteins have the granin consensus sequence these proteins may belong to the secretory proteins. It is currently believed that the BRCA1 and BRCA2 proteins are secreted into milk by the mammary epithelial secretory cells during lactation period. BRCA1 was found in microvilli of apical membrane of mammary epithelial cells. Therefore, the secreted BRCA1 is associated with MFGM. Because of this association, the BRCA1 protein can be detected and quantitated in MFGM by Western immunoblotting with appropriate antibodies and further analyzed by peptide mapping. The BRCA2 protein also be analyzed in MFGM similar to BRCA1.

1. Detection of BRCA1/BRCA2 in Human MFGM by Western Immunoblotting.

100–200 ml of individual milk is used for the preparation of MFGM, as described by Spitsberg et al., 1995, "Association and co-expression of fatty acid binding protein and glycoprotein CD36 in the bovine mammary gland", *Eur J. Biochem.*, vol. 230, 872–878. Briefly, the milk is centrifuged at 1500–1700 times gravity for 15 min. at 5–20 degree C. The "fat cake" (cream layer on the top) is collected and resuspended in 200–500 ml. of distilled $H_2O$ or 10 mM phosphate buffer, pH 7.2 using a Waring blender (about 40–50 sec.), and the mixture is centrifuged at 50,000 times gravity for 1–2 hrs. The pellet of MFGM can be easily collected and stored at −70 degree C. About 5–10 mg of MFGM protein can be obtained from this amount of milk.

As an alternative to the centrifugation step above, it is advantageous to mix the "fat cake" in the 200–500 ml of water or phosphate buffer and to allow it to stand for 24 hours under refrigeration. Following standing, optional filtration to remove lactose is then followed by spray-drying or lyophilization to create a dried concentrate of milk fat globule membranes. Although there is some loss of biological activity following spray-drying and/or lyophilization, enough biological activity remains to allow BRCA1, BRCA2 or other activity assessment of the MFGM.

Detection of BRCA1 and BRCA2 in MFGM is accomplished by Western Immunoblotting as described by Spitsberg et al. (1995), incorporated herein by reference. The anti-human BRCA1 and anti-human BRCA2 can be purchased from Santa Cruz Biotechnology, Inc. (CA, USA).

By detecting levels of BRCA1 and BRCA2 expression in the MFGM in lactating women and tracking the development of breast cancer, a diagnostic test can be established for the propensity for developing breast cancer. Specifically, these proteins are known to act as suppressors of breast cancer. Therefore, a lower than normal expression of BRCA1 would indicate a likelihood of developing breast cancer. Furthermore, the diagnostic test could be taken one step further to the isolation of the proteins from the MFGM to perform activity assays on the isolated proteins to evaluate relative activity. If abnormal expression or activity is determined, the patient could be provided with additional sources of BRCA1 or BRCA2.

2. Protein Microsequencing of BRCA1/BRCA2 of Human MFGM.

Microsequencing analysis of detected BRCA1 and BRCA2 proteins is accomplished according to the procedure described by LeGendre and Matsudaria (1989, Purification of proteins and peptides by SDS-PAGE, in Practical Guide to protein and peptide purification for microsequencing. Ed. D. T. Matsudaria, pp. 49–69), incorporated herein by reference. Briefly, the MFGM proteins, separated by (7.5% gel) SDS/PAGE, are transferred to PVDF membrane and after the identification of BRCA1/BRCA2 bands with Fonceau S staining, the bands are subjected to microsequencing analysis in the gas-phase sequencer (Applied Biosystems Model 470A).

3. Peptide Mapping

Detected BRCA1 BRCA2 can be digested with trypsin or CNBr-treatment. The peptide digest can be analyzed by HPLC ("peptide mapping") (procedure described by LeGendre and Matsudaria, 1989, Purification of proteins and otides by SDS-PAGE, in Practical Guide to protein and peptide purification for microsequencing. Ed. D. T. Matsudaria, pp. 49–69. Comparison of the "peptide maps" from individuals considered to have normal "peptide maps" can provide identification of the individuals with a predisposition to breast cancer.

4. Quantitation of BRCA1 in Human MFGM.

The best mode for quantitation of BRCA1/BRCA2 in human MFGM is Western Immunoblotting rather than by ELISA assay, since it has been found that antibodies to BRCA1 also bind to the nonspecific proteins making ELISA assay less preferable. The quantitation analysis of the proteins by Western Immunoblotting are based on the use of the standard preparation of BRCA1 obtained from the pooled samples of human milk (about 1 liter) or from bovine milk (bovine BRCA1 cross-reacts with anti-human BRCA1) and (2) densitometric analysis of the immunostained BRCA1 protein relative to standard BRCA1 by using an Image Analyzer.

Two primary antibodies against BRCA1 have been used. The first was a mAb against the BRCA1 5' region of exon 11, provided by Dr. W. Lee, and the second was C19-polyclonal antibody provided by Dr. R. Jensen. Both antibodies showed similar immunoblot patterns for the 213 kDa and 160 kDa species in MFGM of cow and human tissue, a weak 220 kDa and prominent 213 kDa band were found, as well as 190 kDA and 160 kDa bands with both antibodies. HRPO-immunostaining intensity of the 220 kDa and 213 kDa species was dependent upon the stage of mammary gland involution. Staining of the 190 kDa protein was not dependent upon involutionary stage. These data show that BRCA1 proteins (about 213 kDa) are present in bovine mammary tissue and are secreted into milk. Their expression also appears related to the physiological state of the mammary gland.

5. Isolation of Bovine MFGM from Milk

The MFGM can be isolated and used as a source of BRCA1 for analysis or for production of large quantities of milk fat globule membranes for incorporation in nutriceuticals, pharmaceutical compositions and foodstuffs. Furthermore, The MFGM is an excellent nutritional supplement. As an example, to isolate the MFGM 1–3 liters of bovine milk is centrifuged at 1500–1700×g for 15 min. at 5–20.degree. C. The "fat cake" (cream layer on the top) is collected and resuspended in 200–500 ml. of distilled $H_2O$ or 10 mM phosphate buffer, pH 7.2 using a Waring blender (about 40–50 sec.). The mixture is placed in the centrifuge at 50,000 times gravity for 1–2-hrs. The pellet of MFGM can be easily collected and stored at −70.degree. C.

As an alternative to the centrifugation step above, it is advantageous to mix the "fat cake" in the 200–500 ml of water or phosphate buffer and to allow it to stand for 24 hours. Following standing, optional filtration to remove lactose is then followed by spray-drying or lyophilization to create a dried concentrate of milk fat globule membranes. This method may be scaled up to dairy production proportions, with proportionately larger amounts of water used for washing. Although there is some loss of biological activity following spray-drying and/or lyophilization, enough biological activity remains to create a useful MFGM composition for incorporation in pharmaceutical compositions, foodstuffs or nutriceutical compositions.

The phosphorylation of the MFGM proteins can be increased. As an example of the method of phosphorylation, 100 mg of MFGM proteins are mixed with ATP in concentration 10–20 mM and $MgCl_2$ (5 mM) is added. The mixture is incubated 30 minutes at room temperature, and placed in the centrifuge at 50,000.times.g for 30 minutes (cold 4–10 degrees C.). The pellet of the phosphorylated MFGM proteins can be collected and stored at −70.degree. C.

The MFGM proteins can be incorporated into all the milk market commodities (cheese, fluid milk, butter, frozen desserts, bakery, confections, etc.) or incorporated into a tablet or capsule for use as a nutritional supplement. The MFGM is predominantly separated from the fat, so it is a good source of protein with the additional benefits of providing the proteins in the MFGM known to act as suppressors of cancers.

6. Isolation of BRCA1 from MFGM and Mammary Gland Tissues of Lactating Animals

Milk and mammary gland tissue from lactating animals are rich sources of BRCA1. BRCA1 can be isolated and purified by conventional chromatographic methods, including but not limited to, gel-filtration, HPLC, etc. Isolated BRCA1 can be used for scientific purposes and for the treatment of breast cancer. Limited proteolytic digestion of BRCA1 protein can release the active form of small peptides, which can be easily purified by HPLC. These peptides can be used as a therapeutic agents for the treatment of breast cancer.

Accordingly, the method of the invention includes channeling un-pasteurized fluid milk through a pasteurizer (high temperature, short time). The milk remains un-homogenized and is whipped into two phases. Phase 1 is the (cream) and phase 2 is the aqueous phase. The cream is collected manually and washed in sterile water (2–8 degrees Celcius) for 24 hours. After 24 hours, the aqueous phase is collected and passed through a microfilter device to remove lactose. After lactose removal, the aqueous phase is collected and dried using spray drying. The amounts of water are not critical for the 24 hour washing step and may comprise anywhere from about 1/10 to about 100 times the volume of the cream phase to be washed. The temperature for the 24-hour washing step may range between about 2–8 degrees C. and is preferably 4 degrees C. The 24-hour period itself may be varied from about 15 hours to about 36 hours. By washing, the cream is mixed with and allowed to stand quiescently or is gently mixed continuously or sporadically during the washing period.

MFGM, obtained from the procedure described above, can be weighed and added to various foodstuffs, vitamins, etc. An example is given below.

Example 1

Milk casein powder, whey powder, wheat agglutinin, artificial sweetener, and artificial flavoring is added to various amounts of MFGM and mixed, after mixing these powders are added to bottles. A portion of this powder can then be added to skim milk. The skim milk is homogenized in a small blender. The material may be consumed as a beverage.

Although the invention has been described with particularity above, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

I claim:

1. A method for separating milk fat globule membranes from milk, comprising the steps of pasteurizing a quantity of unhomogenized milk; whipping the unhomogenized milk thus pasteurized into a cream phase and a first aqueous phase; separating the cream phase and washing the cream phase with water over about 15–36 hours to create a second aqueous phase; and drying said second aqueous phase to yield a preparation containing milk fat globule membranes.

2. The method according to claim 1 wherein the washing step takes place over about 24 hours.

3. The method according to claim 1 wherein the washing step is conducted at 2–8 degrees C.

4. The method according to claim 1 wherein the milk is human milk to be assessed for diagnostic purposes.

5. The method according to claim 1 wherein the milk is dairy milk to be separated for commercial purposes.

6. The method according to claim 1 wherein said drying step further comprises spray drying.

7. The method according to claim 1 wherein said drying step further comprises lyophilization.

8. The method according to claim 1 wherein the cream phase is washed in about $1/10$–100 times its volume of distilled water.

9. The method according to claim 1 wherein the cream phase is washed in about $1/10$–100 times its volume of sterile water.

* * * * *

UNITED STATES PATENT AND TRADEMARK OFFICE
CERTIFICATE OF CORRECTION

PATENT NO.   : 6,391,362 B1
DATED        : May 21, 2002
INVENTOR(S)  : Ronald C. Gorewit It is certified that error appears in the above-identified patent and that said Letters Patent is hereby corrected as shown below:

Column 1,
Line 6, "09/236,90" should read -- 09/236,906 --.
Line 6, "affirmed" should read -- filed --.
Line 10, "Ser. No. 5,905,026" should read -- Pat. No. 5,905,026 --.

Column 3,
Line 4, "BRCA2protein" should read -- BRCA2 protein --.

Column 5,
Line 12, after "This invention" insert "dramatically".

Column 6,
Line 58, between "BRCA1" and "BRCA2" insert -- / --.

Signed and Sealed this

Twenty-ninth Day of October, 2002

Attest:

JAMES E. ROGAN
Attesting Officer
Director of the United States Patent and Trademark Office